(12) United States Patent
Chang

(10) Patent No.: US 6,730,098 B2
(45) Date of Patent: May 4, 2004

(54) TISSUE REMOVAL PEN

(76) Inventor: Henry Ping Chang, 2690 E. California Blvd., San Marino, CA (US) 91108

( * ) Notice: Subject to any disclaimer, the term of this patent is extended or adjusted under 35 U.S.C. 154(b) by 243 days.

(21) Appl. No.: 10/096,974

(22) Filed: Mar. 14, 2002

(65) Prior Publication Data

US 2003/0187462 A1 Oct. 2, 2003

(51) Int. Cl.⁷ ............................................... A61B 17/50
(52) U.S. Cl. .................................................... 606/131
(58) Field of Search ............................... 606/131–134; 604/289, 290

(56) References Cited

U.S. PATENT DOCUMENTS 4,378,804 A * 4/1983 Cortese, Jr. ................ 606/131
6,306,119 B1 * 10/2001 Weber et al. ............... 606/131
6,629,983 B1 * 10/2003 Ignon ......................... 606/131

* cited by examiner

*Primary Examiner*—Kevin T. Truong
(74) *Attorney, Agent, or Firm*—Raymond Y. Chan; David and Raymond Patent Group

(57) ABSTRACT

A tissue removal pen includes a pen body having a working end and a handle portion, and an abrasion unit, which is mounted on the pen body, including an abrasion head extended outwardly from the working end of the pen body for removing cells from a treating skin surface of a user. A collecting unit includes a collecting conduit, which is mounted on the pen body, having a discharging end and an intake end extended toward the working end, and a collecting head replaceably mounted to the intake end of the collecting conduit and extended from the working end of the pen body to a position that adjacent to the abrasion head of the abrasion unit. A vacuuming source is connected to the discharging end of the collecting conduit to provide a reduced pressure within the collecting head for collecting cells removed from the treating skin surface.

20 Claims, 7 Drawing Sheets

TISSUE REMOVAL PEN

BACKGROUND OF THE PRESENT INVENTION

1. Field of Invention

The present invention relates to skin treatment tool, and more particularly to a tissue removal pen for removing dead and old skin cells on an epidermis of a patient to provide a revitalized, fresh skin surface.

2. Description of Related Arts

The removal of the epidermis of a user has been used to provide softer skin for years. A conventional apparatus for microdermabrasion is used to scrub the epidermis of the user such that dead and old skin cells are abraded off the epidermis of the user.

However, such conventional apparatus has several drawbacks. For example, U.S. Pat. No. 6,241,739 generally discloses a microdermabrasion device comprising a hollow tube having an abrasive treatment ring tip provided at a free end of the hollow tube for dislodging cells from the surface being treated and a vacuum source attached to the tube for applying the reduced pressure within the hollow tube so as to collect the cells from the abrasive treatment ring tip through the hollow tube. Accordingly, the hollow tube has a central opening defining at the abrasive treatment ring tip for sucking the dislodged cell on the surface of the skin and a grinding surface formed at the circumference of the abrasive treatment ring tip at the central opening in such a manner that the cells on the surface of the skin is abraded off by the grinding surface and collected from the central opening.

However, when operating the microdermabrasion device, a portion of the skin is swollen out at the central opening. Due to the swollen portion of the skin, the grinding surface of the abrasive treatment ring tip cannot fittedly contact with the surface of the skin. In other words, the dead and old cells may not be entirely scrubbed out of the surface of the skin. Moreover, when the grinding surface of the abrasive treatment ring tip is grinding on the bumpy surface of the skin, the healthy cells or tissues on the skin will also be abraded off to damage the skin, which can be infectious.

Furthermore, due to the difficult tissue structure of the human body, the microdermabrasion device cannot apply on some non-abrasive skin areas of the face, such as the skin areas around the eye or the mouth. Since the abrasive treatment ring tip of the hollow tube works as an abrasive tool and a sucking tool, the abrasive treatment ring tip cannot provide a fine movement of the skin surface of the user, especially while the grinding surface of the abrasive treatment ring tip is contacting around the non-abrasive skin area.

In other words, since the sucking area of the abrasive treatment ring tip (i.e. the central opening) is positioned within the grinding area of the abrasive treatment ring tip (i.e. the grinding surface), the movement of the sucking area of the abrasive treatment ring tip on the skin surface is restricted by the grinding area thereof. Therefore, it is difficult for the user to control the abrasive treatment ring tip in order to prevent the excessive abrasion of the skin surface and damage the skin.

As a result, the abrasive treatment ring tip cannot provide a precise grinding area on the surface being treated by the ring-shaped grinding surface. Moreover, since the sucking area of the abrasive treatment ring tip is positioned within the grinding area of the abrasive treatment ring tip, the cells dislodged from the skin may split out of the abrasive treatment ring tip since the sucking area may not have enough sucking power to suck the cells dislodged from the skin.

SUMMARY OF THE PRESENT INVENTION

A main object of the present invention is to provide a tissue removal pen is to minimize the grinding area thereof, so as to provide a fine grinding movement to precisely remove dead and old skin cells on an epidermis of a patient to provide a revitalized, fresh skin surface.

Another object of the present invention is to provide a tissue removal pen wherein an abrasion head and a collecting head of the removal pen are replaceable individually such that the user can select the proper abrasion head and collecting head to effectively remove the cells on the treating skin surface. In other words, the user is able to select a tapered shaped abrasion head to provide a fine and precise grinding movement or an abrasion head having a flat grinding surface to enlarge the area of the treating skin surface to be abraded.

Another object of the present invention is to provide a tissue removal pen wherein the collecting head is positioned adjacent to the abrasion head for collecting cells removed from the treating skin surface by means of vacuum effect. Therefore, the user is able to precisely control the abrasion head of the tissue removal pen on the treating skin surface to remove the cells thereon without interrupting by the collecting head of the tissue removal.

Another object of the present invention is to provide a tissue removal pen wherein the area of the treating skin surface to be abraded is positioned within the area of the treating skin surface to be collected in such a manner that after the cells are removed by the abrasion head, the collecting head of the tissue removal pen can effectively vacuum the removed cells on the treating skin surface so as to prevent the removed cell from dispensing in the surrounding air.

Another object of the present invention is to provide a tissue removal pen wherein the abrasion head is adapted to be powered by a motor assembly to provide an abrasive movement for effectively removing the cells on the treating skin surface.

Accordingly, in order to accomplish the above objects, the present invention provides a tissue removal pen, comprising:

a pen body having a working end and a handle portion;

an abrasion unit, which is mounted on the pen body, comprising a solid abrasion head extended outwardly from the working end of the pen, wherein the abrasion head has top coupling end, a bottom scrubbing end, and an abrasion body solidly extended from the coupling end to the scrubbing end, the abrasion head further having a periphery bottom edge surrounding at the scrubbing end and a scrubbing surface defined within the periphery bottom edge for removing cells from a treating skin surface of a user;

a collecting unit comprising a collecting conduit, which is extended along the pen body, having a discharging end and an intake end extended toward the working end, and a collecting head replaceably mounted to the intake end of the collecting conduit and extended from the working end of the pen body to a position that adjacent to the scrubbing surface of the abrasion head of the abrasion unit; and a vacuuming source connected to the discharging end of the collecting conduit to provide a reduced pressure within the collecting head for collecting cells removed from the treating skin surface.

DETAILED DESCRIPTION OF THE PREFERRED EMBODIMENT

Figure 1:
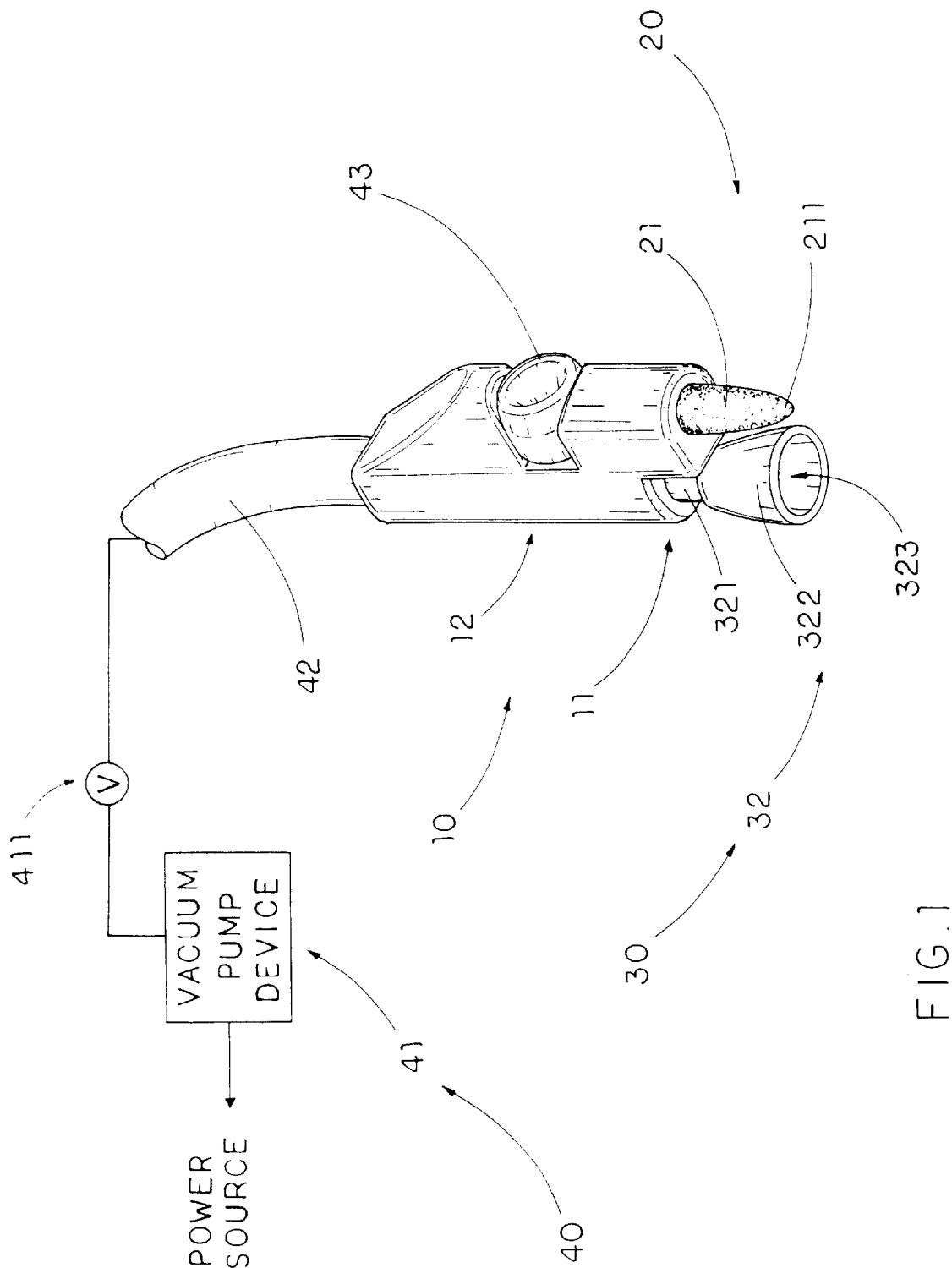
FIG. 1 is a perspective view of a tissue removal pen according to a first preferred embodiment of the present invention.
Figure 2:
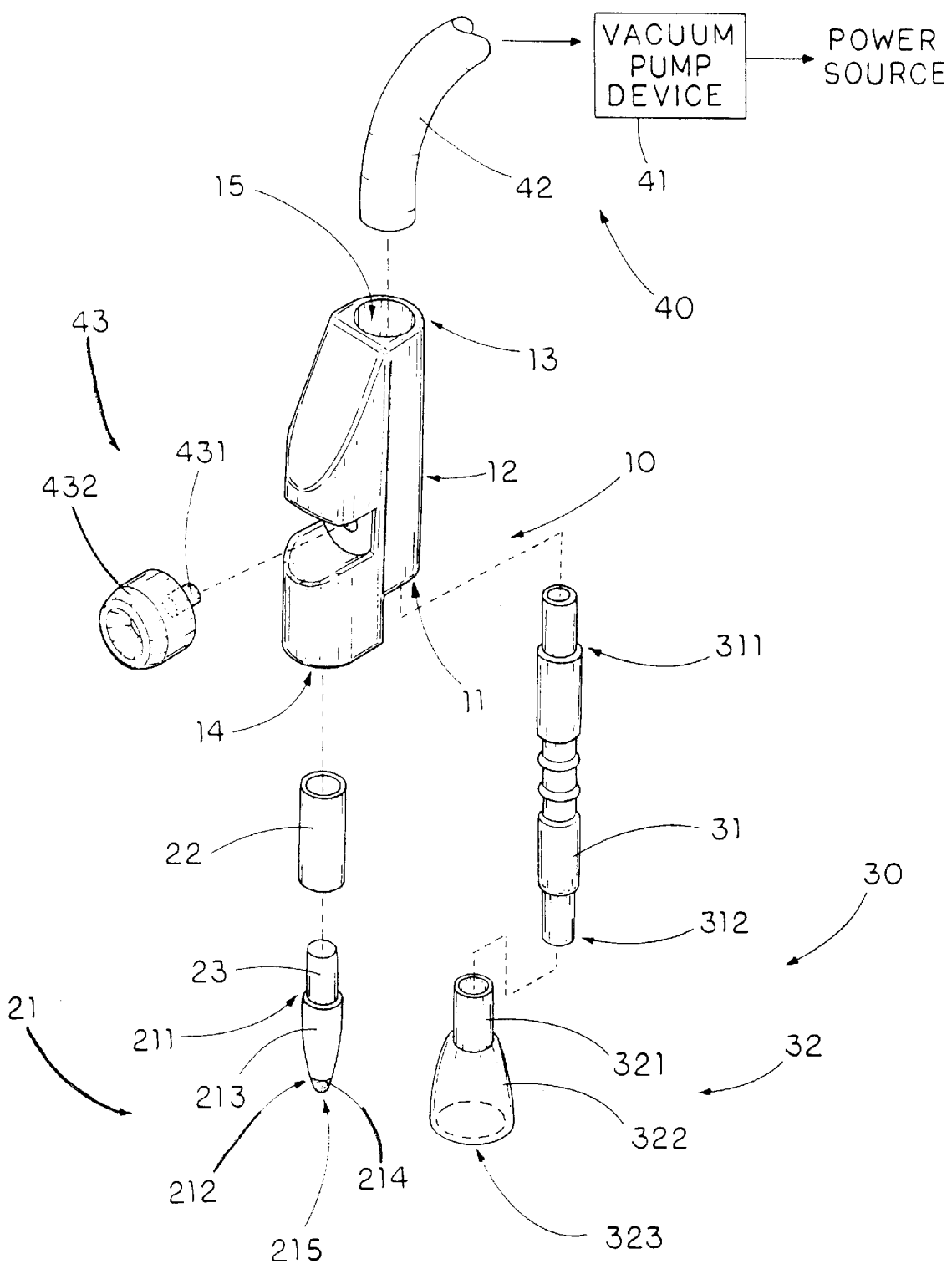
FIG. 2 is an exploded perspective view of the tissue removal pen according to the above first preferred embodiment of the present invention.

Referring to FIGS. 1 and 2 of the drawings, a tissue removal pen according to a first preferred embodiment of the present invention is illustrated, wherein the tissue removal pen comprises a pen body 10 having a working end 11 and a handle portion 12 and an abrasion unit 20 comprising an abrasion head 21 replaceably mounted to the working end 11 of the pen body 10 for removing cells from a treating skin surface of a user, wherein the treating skin surface is referred to as the epidermis.

The tissue removal pen further comprises a collecting unit 30 comprising a collecting conduit 31, which is extended along the pen body 10, having an discharging end 311 and an intake end 312 extended toward the working end 11 of the pen body 10, and a collecting head 32 replaceably mounted to the intake end 312 of the collecting conduit 31 and extended from the working end 11 of the pen body 10 to a position that adjacent to the abrasion head 21 of the abrasion unit 20.

A vacuuming source 40 is coupled with the discharging end 311 of the collecting conduit 31 to provide a reduced pressure with the collecting head 32 for collecting cells removed from the treating skin surface.

According to the preferred embodiment, the pen body 10 has an elongated body having the working end 11 and an opposed connecting end 13 wherein the handle portion 13 of the pen body 10 is formed between the working end 11 and the connecting end 13 for easy gripping by the user. The pen body 10 further has an abrasive cavity 14 longitudinally provided at the working end 11 of the pen body 10 and an elongated holding slot 15 extended between the working end 11 of the pen body 10 and the connecting end 13 thereof.

The abrasion head 21 has top coupling end 211, a bottom scrubbing end 212, and an abrasion body 213 solidly extended from the coupling end 211 to the scrubbing end 212. The abrasion head 21 further having a periphery bottom edge 214 surrounding at the scrubbing end 212 and a scrubbing surface 215 defined within the periphery bottom edge 214 for removing cells from the treating skin surface of the user.

The scrubbing surface 215 of the abrasion head 21 is arranged for contacting with the treating skin surface so as to remove the cells thereon. The abrasion head 21 is made of scrubbing material, such as diamond grit or aluminum oxide, adapted for abrading on the treating skin surface to remove the dead and old cells thereon. Alternatively, the scrubbing end 212 of the abrasion head 21 is made of the scrubbing material to form the scrubbing surface 215 in order to scrub on the treating skin surface. Other scrubbing materials such as silicon carbide, silicon, or various nitrate metals can be used to form the scrubbing surface 215 of the abrasion head 21. Accordingly, the abrasion head 21 is adapted to be shaped to form the scrubbing surface 215 having a tapered shaped to remove the cells on the treating skin surface in a fine movement. The abrasion head 21 is shaped to form the scrubbing surface 215 having a flat surface for enlarging the scrubbing area of the scrubbing surface 215.

Figure 3A:
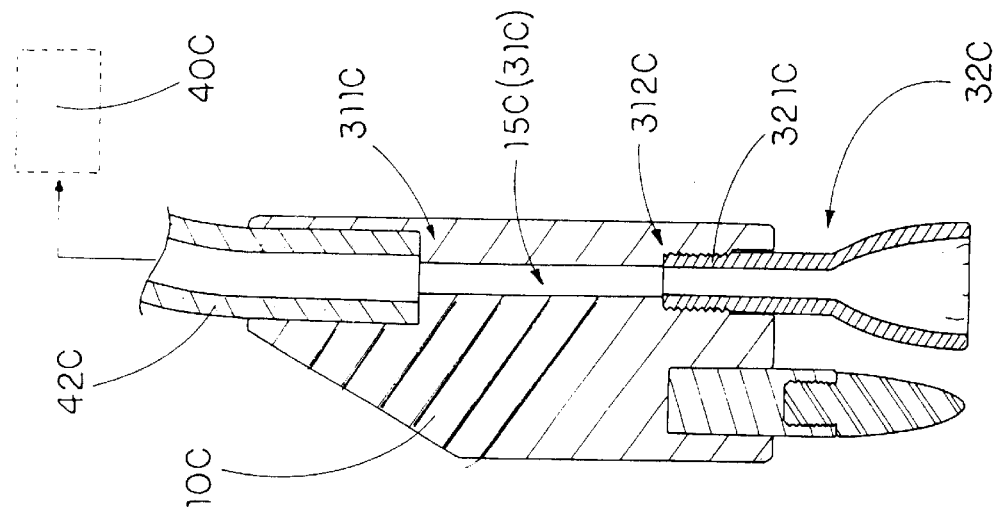
FIG. 3A illustrates an alternative mode of a collecting conduit of the tissue removal pen according to the above first preferred embodiment of the present invention.
Figure 3:
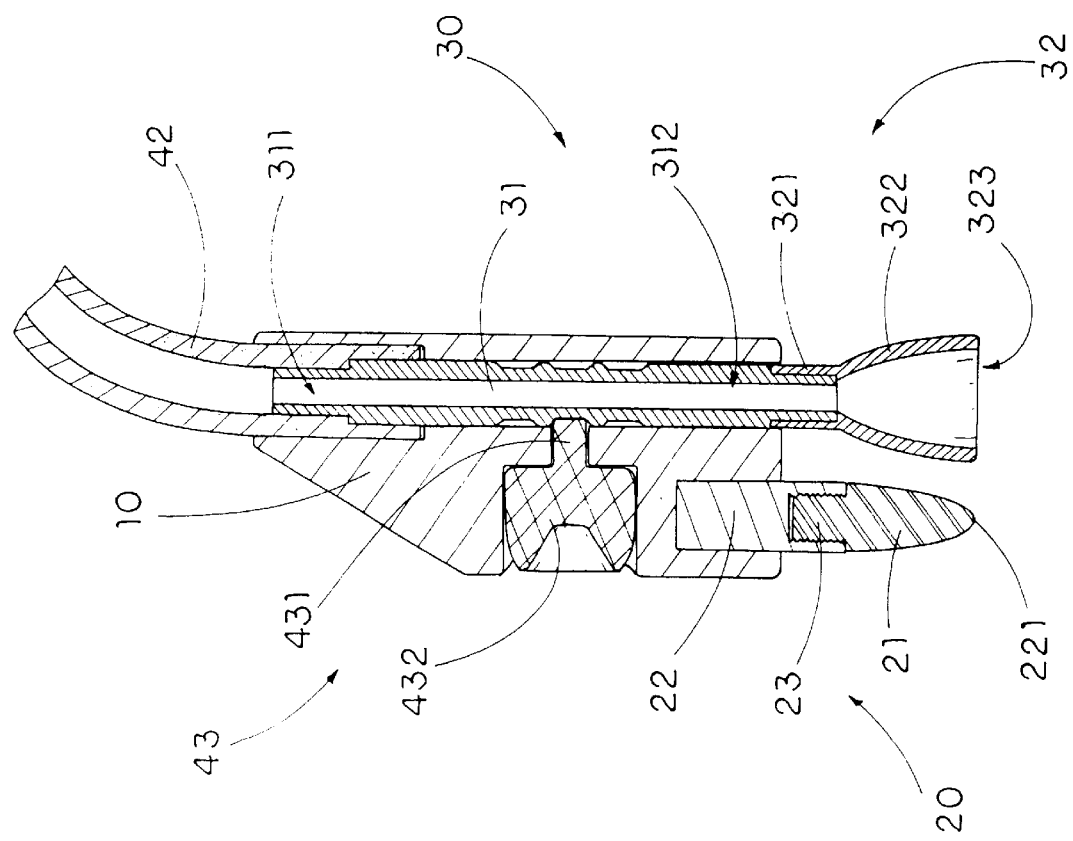
FIG. 3 is a sectional view of the tissue removal pen according to the above first preferred embodiment of the present invention.

As shown in FIG. 3, the abrasion unit 20 further comprises an abrasive socket 22 firmly received in the abrasive cavity 14 of the pen body 10 wherein the abrasion head 21 comprises a receiving plug 23 provided at the coupling end 211 of the abrasion body 213 and detachably inserted into the abrasive socket 22 in such a manner that the abrasion head 21 is replaceably mounted to the pen body 10. It is worth to mention that in order to provide different scrubbing levels, the abrasion head 21 can be made of the scrubbing material to provide a coarse scrubbing surface 215 for removing the cells on the treating skin surface rapidly or a fine scrubbing surface 215 for deep cleaning the treating skin surface and functioning in a polishing manner. In other words, the user is able to exchange the proper abrasion head 21 to achieve a desired scrubbing effect.

The collecting conduit 31, which is an elongated flexible tube, is disposed in the holding slot 15 wherein the discharging end 311 of the collecting conduit 31 is extended toward the connecting end 13 of the pen body 10 and the intake end 312 of the collecting conduit 31 is extended toward the working end 11 of the pen body 10. In other words, the collecting conduit 31 is enclosed in the pen body 10.

According to the preferred embodiment, the collecting head 32 has an adapter portion 321 detachably mounted to the intake end 312 of the collecting conduit 31 and a cup portion 322 having a bottom sucking opening 323 communicating with the intake end 312 of the collecting conduit 31 through the adapter portion 321 for collecting the cells from the treating skin surface. Accordingly, the cup portion 322 of the collecting head 32 has a bell shape to enlarge the sucking opening 323 for enhancing the sucking area of the collecting head 32 on the treating skin surface.

Accordingly, a filter unit should be incorporated with the collecting unit 30 for collecting cells removed from the treating skin surface wherein the filter unit is replaceably mounted to the collecting unit 30 at a position before the removed cells vacuuming to the vacuuming source 40 so that all the cells removed from the treating skin surface are trapped by the filter unit so as to prevent the removed cells and/or collected body oils entering the vacuuming source 40.

The vacuuming source 40 comprises a vacuum pump device 41 electrically connected to a power source and an extension tube 42 connected the vacuum pump device 41 to the discharging end 311 of the collecting conduit 31 in such a manner that the vacuum pump device 41 is arranged to provide the reduced pressure through the sucking opening 323 of the collecting head 32 for collecting the cells from the treating skin surface by means of vacuum effect.

The vacuuming source 40 further comprises a control switch 43 operatively mounted on the pen body 10 for controlling a pressure through the sucking opening 323 of the collecting head 32. Accordingly, the control switch 43 comprises a pusher arm 431 transversely mounted on the pen body 10 in a slidably movable manner for transversely biasing against the collecting conduit 31 and a switch body 432 extended from the pusher arm 431 for driving the pusher arm 432 to a position that when the pusher arm 431 is moved toward the collecting conduit 31 to bias against the collecting conduit 31, the pressure through the sucking opening 323 is reduced, and when the pusher arm 431 is moved away from the collecting conduit 31, the pressure through the sucking opening 323 is increased. Accordingly, there different levels, which are high pressure, low pressure, and off, of the reduced pressure through the sucking opening 323 of the collecting conduit 32 can be selectively controlled by the control switch 43 on the pen body 10 for easy operation without switching on the vacuum pump device 41. Of course, a pressure gauge 411 is adapted to be incorporated with the vacuum pump device 41 for controlling an initial pressure to the collecting unit 30.

FIG. 3A illustrates an alternative mode of the collecting conduit 31C. The holding slot 15C of the pen body 10C functions as the collecting conduit 31C wherein a top opening of the holding slot 15C is embodied as the discharging end 311C of the collecting conduit 31C to detachably connect the extension 42C of the vacuuming source 40C and a bottom opening of the holding slot 15C is embodied as the intake end 312C to detachably connect the adapter portion 321C of the collecting head 32C. In other words, no external collecting conduit 31C is needed to mount along the pen body 10C in order to communicate the vacuuming source 40C with the collecting head 32C.

Figures 4A, 4B:
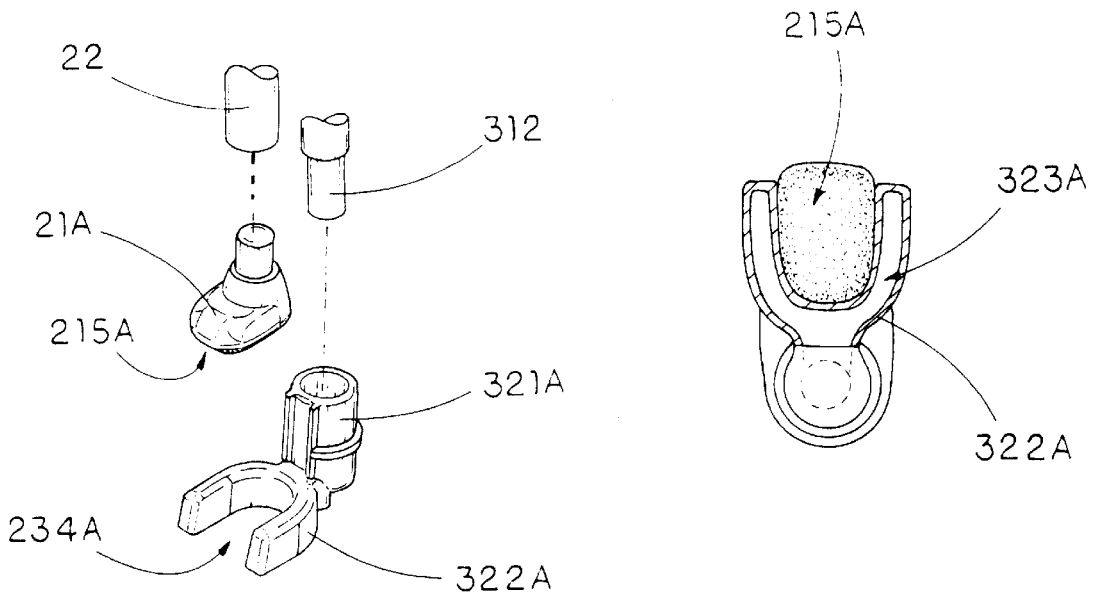
FIGS. 4A and 4B illustrate a first alternative mode of a collecting head of the tissue removal pen according to the above first preferred embodiment of the present invention.

FIG. 4A illustrates a first alternative mode of the collecting head 32A which has an adapter portion 321A detachably mounted to the intake end 312 of the collecting conduit 31 and a cup portion 322A having a bottom sucking opening 323A communicating with the intake end 312 of the collecting conduit 31 through the adapter portion 321A for collecting the cells from the treating skin surface.

Referring to FIG. 4B, the cup portion 322A has a U-shaped structure to form the U-shaped sucking opening 323A to define a receiving space 234A wherein the scrubbing surface 215A of the abrasion head 21A is positioned within the receiving space 324A. Therefore, the area of the sucking opening 323A of the collecting head 32A is enlarged to cover larger collecting area of the treating skin surface.

Figures 5A, 5B:
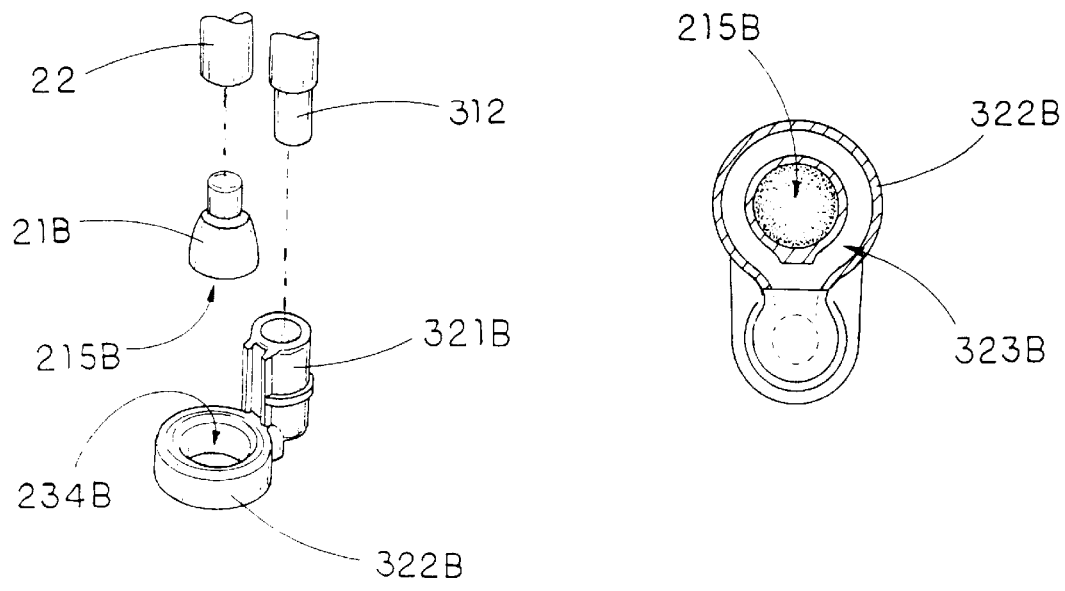
FIGS. 5A and 5B illustrate a second alternative mode of the collecting head of the tissue removal pen according to the above first preferred embodiment of the present invention.

FIG. 5A illustrates a second alternative mode of the collecting head 32B which has an adapter portion 321B detachably mounted to the intake end 312 of the collecting conduit 31 and a cup portion 322B having a bottom sucking opening 323B communicating with the intake end 312 of the collecting conduit 31 through the adapter portion 321B for collecting the cells from the treating skin surface.

Referring to FIG. 5B, the cup portion 322B has a ring-shaped structure to form the circular sucking opening 323B to define a receiving space 234B wherein the scrubbing surface 215B of the abrasion head 21B is coaxially positioned within the receiving space 234B.

It is worth to mention that the scrubbing surface 215 of the abrasion head 21, according to the first and second alternative modes, is positioned within the sucking opening 323A, 323B of the collecting head 32A, 32B, such that when the cells are removed from the treating skin surface, the removed cells are collected through the sucking opening 323A, 323B, so as to prevent the removed cells from dispensing to the surrounding air. Moreover, the area of the treating skin surface is forced to swollen at the sucking opening 323A, 323B of the collecting head 32A, 32B is enlarged to enhance the scrubbing surface 215 of the abrasion head 21 in contact with treating skin surface.

Figure 6:
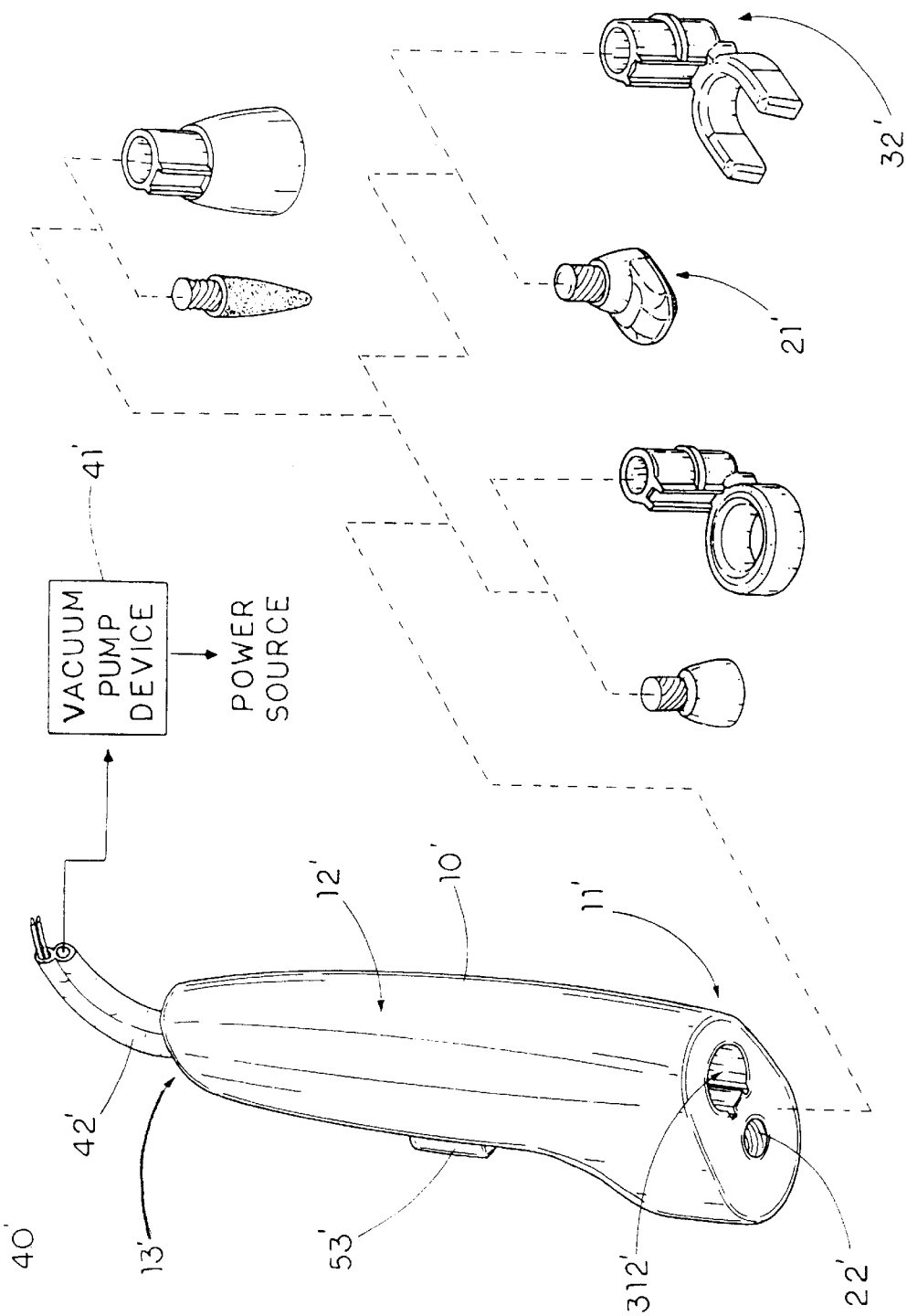
FIG. 6 is a perspective view of a tissue removal pen according to a second preferred embodiment of the present invention.
Figure 7:
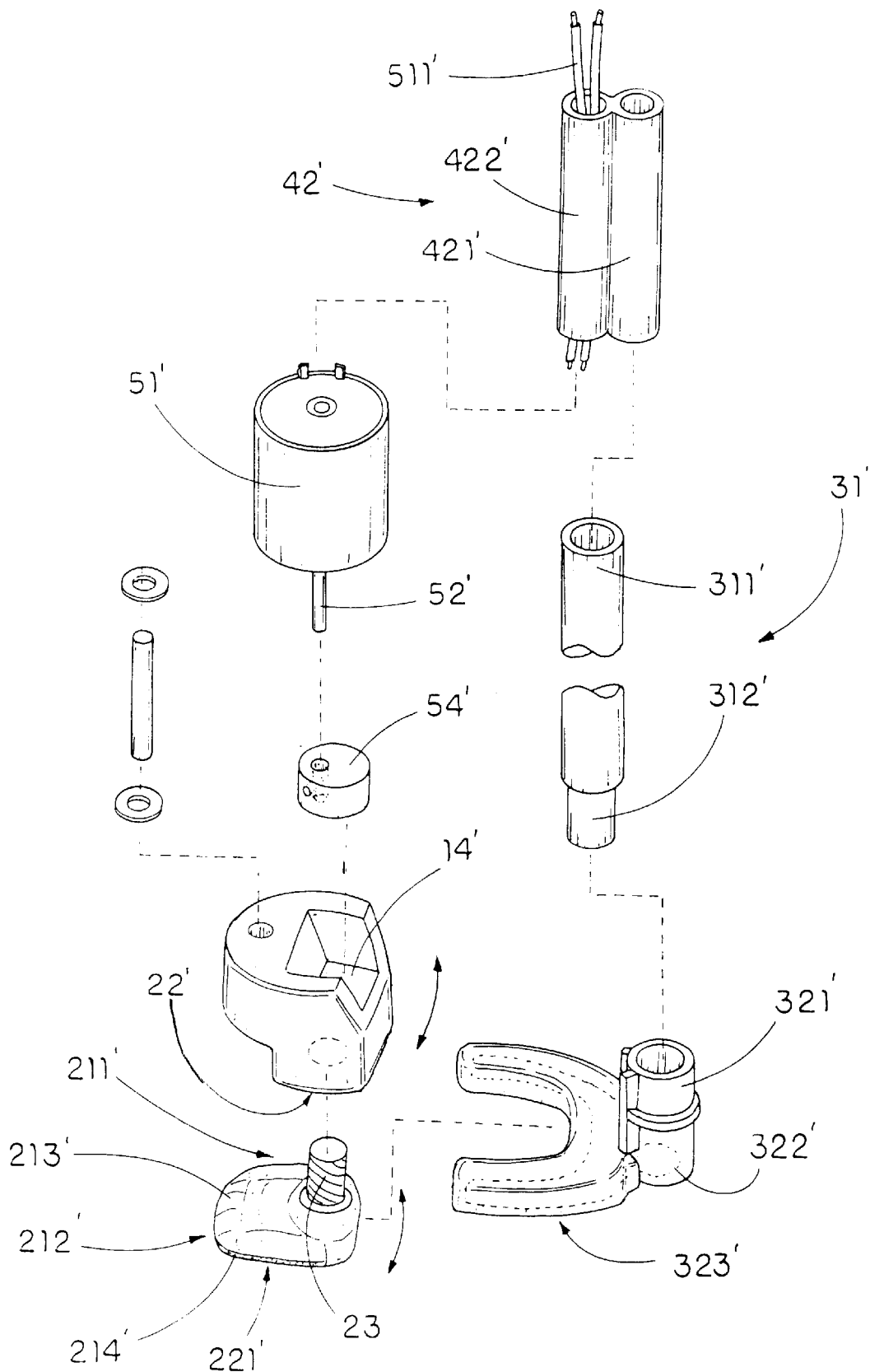
FIG. 7 is a partially exploded perspective view of the tissue removal pen according to the above second preferred embodiment of the present invention.

Referring to FIGS. 6 and 7, a second embodiment of the tissue removal pen illustrates an alternative mode of the first embodiment of the present invention, wherein the tissue removal pen of the second embodiment is incorporated with a motor assembly 50' such that the abrasion unit 20' is powered by the motor assembly 50' to provide an abrasion movement of the abrasion head 21'.

Figure 8:
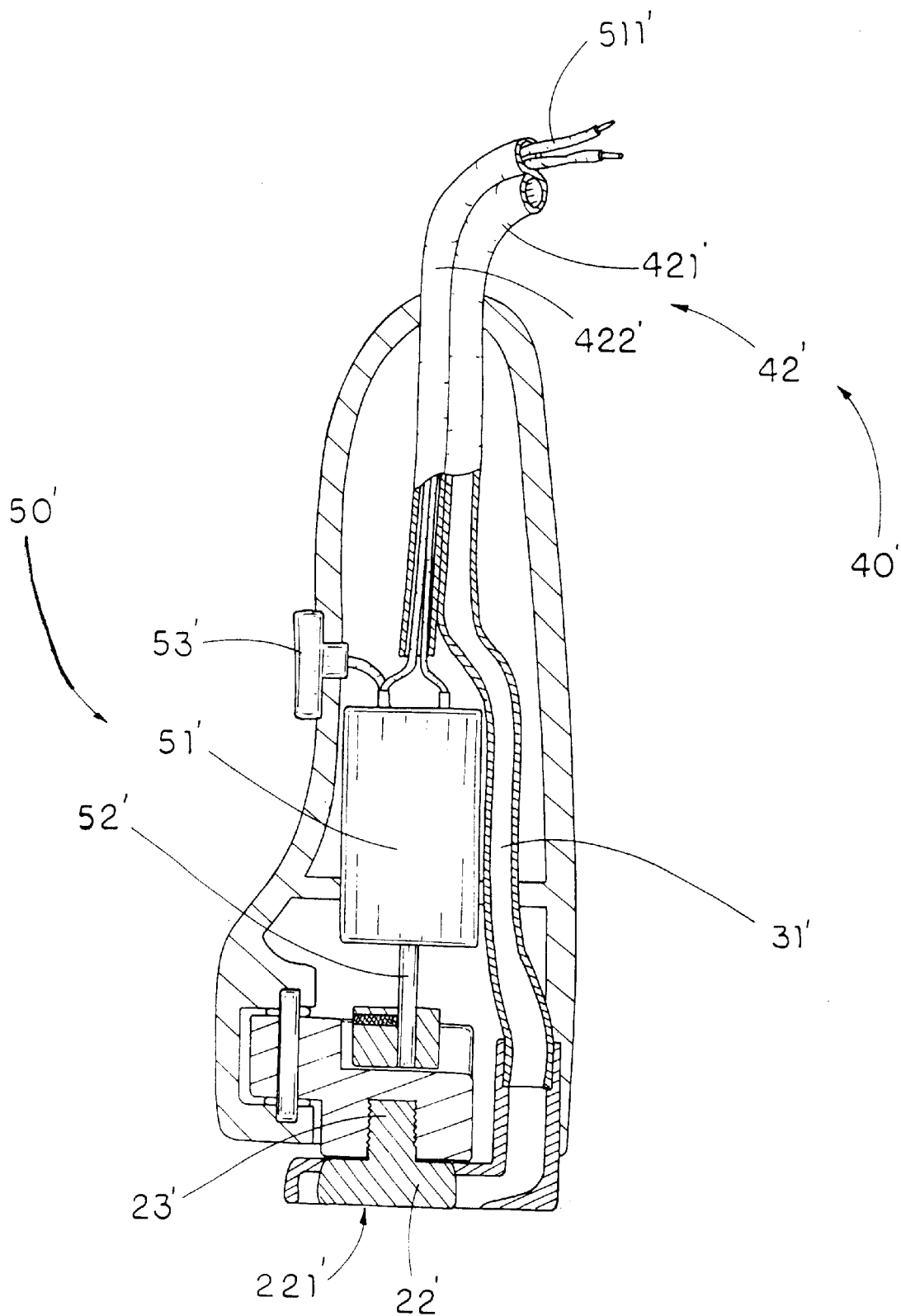
FIG. 8 is a sectional view of the tissue removal pen according to the above second preferred embodiment of the present invention.

As shown in FIGS. 7 and 8, the tissue removal pen comprises a pen body 10' having a working end 11' and a handle portion 12'. The pen body 10' further has an abrasive cavity 14' longitudinally provided at the working end 11' of the pen body 10' and an elongated holding slot 15' extended from the working end 11 of the pen body 10' to the connecting end 13' thereof. The pen body 10' further has a motor cavity 16' provided therein.

An abrasion unit 20', which is extended outwardly from the working end 11' of the pen body 10', has top coupling end 211', a bottom scrubbing end 212', and an abrasion body 213' solidly extended from the coupling end 211' to the scrubbing end 212'. The abrasion head 21' further having a periphery bottom edge 214' surrounding at the scrubbing end 212' and a scrubbing surface 215' defined within the periphery bottom edge 214' for removing cells from the treating skin surface of the user.

The abrasion unit 20' further comprises an abrasive socket 22' firmly received in the abrasive cavity 14' of the pen body 10' wherein the abrasion head 21' comprises a receiving plug 23' detachably inserted into the abrasive socket 22' in such a manner that the abrasion head 21' is replaceably mounted to the pen body 10'.

A collecting unit 30' comprises a collecting conduit 31', which is mounted on the pen body 10', having an discharging end 311' and an intake end 312' extended toward the working end 11' of the pen body 10', and a collecting head 32' replaceably mounted to the intake end 312' of the collecting conduit 31' and extended from the working end 11' of the pen body 10' to a position that adjacent to the abrasion head 21' of the abrasion unit 20'.

A vacuuming source 40' is connected to the discharging end 311' of the collecting conduit 31' to provide a reduced pressure with the collecting head 32' for collecting cells removed from the treating skin surface. The vacuuming source 40' comprises a vacuum pump device 41' and an extension tube 42' connected the vacuum pump device 41' to the discharging end 311' of the collecting conduit 31' in such a manner that the vacuum pump device 41' is arranged to provide the reduced pressure through the sucking opening 323' of the collecting head 32' for collecting the cells from the treating skin surface by means of vacuum effect.

The motor assembly 50' comprises a motor 51' securely supported in the motor cavity 16' of the pen body 10' and electrically connected to a power source via a conductive wire 511' and a motor shaft 52' operatively extended from the motor 51' to the abrasion head 21' so as to provide the abrasion movement of the scrubbing surface 215' thereof. Accordingly, the abrasion movement can be a circular movement, a swinging movement, or other movement that can enhance the scrubbing effect to remove the cells from the treating skin surface. For example, the motor 51' should provide a swinging abrasion movement for the abrasion head 32A when it is used as shown in FIG. 4A. Alternatively, when the abrasion head 32 is used as shown in FIG. 3, the preferred abrasion movement should be in a circular manner.

The motor assembly 50' further comprises a switch button 53' provided on the pen body 10' for switching the motor 51' on and off and a movable manner 54', having a bearing installed thereinto, non-coaxially mounted on the motor shaft 52' for providing the swinging abrasion movement of the abrasion head 21' through the motor 51'.

As shown in FIG. 7, the extension tube 42' is constructed by two tubular holders 421', 422' integrally extended side by side wherein the first tubular holder 421' is integrally connected to the discharging end 311' of the collecting conduit 31' for communicating the vacuum pump device 41' with the collecting head 32' and the conductive wire 511' is passing through the second tubular holder 422' from the motor 51' to the power source so as to protect the conductive wire 511' from being damaged.

It is worth to mention that both the abrasion head 21' and the collecting head 32' are replaceable and can be shaped to fit the need thereof. Moreover, the collecting head 32' is adapted to be shaped as a bell shape, U-shaped, or ring-shaped, as shown in FIGS. 1 through 5 of the first embodiment, so as to enhance the abrasive effect of the tissue removal pen.

What is claimed is:

1. A tissue removal pen, comprising:

a pen body having a working end and a handle portion;

an abrasion unit comprising an abrasion head replaceably mounted to said working end of said pen body, wherein said abrasion head has top coupling end, a bottom scrubbing end, and an abrasion body solidly extended from said coupling end to said scrubbing end, said abrasion head further having a periphery bottom edge surrounding at said scrubbing end and a scrubbing surface defined within said periphery bottom edge for removing cells from a treating skin surface of a user;

a collecting unit comprising a collecting conduit, which is extended along said pen body, having an intake end extended toward said working end, and a collecting head, having a bottom sucking opening, replaceably mounted to said intake end of said collecting conduit wherein said collecting head is extended from said working end of said pen body to a position that said sucking opening is adjacent to said scrubbing surface of said abrasion head of said abrasion unit; and a vacuuming source coupled with said discharging end of said collecting conduit to provide a reduced pressure within said collecting head for collecting cells removed from the treating skin surface through said sucking opening.

2. A tissue removal pen, as recited in claim 1, wherein said abrasion unit further comprises an abrasive socket firmly affixed to said working end of said pen body and wherein said abrasion head comprises a receiving plug provided at said coupling end of said abrasion body and detachably inserted into said abrasive socket so as to replaceably mount said abrasion head on said pen body.

3. A tissue removal pen, as recited in claim 2, wherein said collecting head has an adapter portion detachably mounted to said intake end of said collecting conduit and a cup portion having a bell-shaped to form said sucking opening having an enlarged circular sucking area, wherein said scrubbing surface of said abrasion head is positioned adjacent to said sucking opening.

4. A tissue removal pen, as recited in claim 2, wherein said collecting head has an adapter portion detachably mounted to said intake end of said collecting conduit and a cup portion shaped to form said sucking opening having an U-shaped structure so as to define a receiving space, wherein said scrubbing surface of said abrasion head is positioned within said receiving space.

5. A tissue removal pen, as recited in claim 4, wherein said vacuuming source comprises a vacuum pump device and an extension tube connected said vacuum pump device to a discharging end of said collecting conduit in such a manner that said vacuum pump device is arranged to provide said reduced pressure through said sucking opening of said collecting head for collecting said cells from said treating skin surface.

6. A tissue removal pen, as recited in claim 5, further comprising a motor assembly comprising a motor securely supported in said pen body and electrically connected to a power source via a conductive wire and a motor shaft operatively extended from said motor to said abrasion head, so as to provide an abrasion movement of said scrubbing surface of said abrasion head.

7. A tissue removal pen, as recited in claim 6, wherein said extension tube is constructed by two tubular holders integrally extended side by side wherein said first tubular holder is integrally connected to said discharging end of said collecting conduit for communicating said vacuum pump device with said collecting head, and wherein said conductive wire is extended from said motor to said power source through said second tubular holder.

8. A tissue removal pen, as recited in claim 4, wherein said vacuuming source further comprises a control switch comprising a pusher arm transversely mounted on said pen body in a slidably movable manner for transversely biasing against said collecting conduit and a switch body extended from said pusher arm for driving said pusher to a position that when said pusher arm is moved toward said collecting conduit to bias against said collecting conduit, a pressure through said sucking opening is reduced, and when said pusher arm is moved away from said collecting conduit, said pressure through said sucking opening is increased.

9. A tissue removal pen, as recited in claim 2, wherein said collecting head has an adapter portion detachably mounted to said intake end of said collecting conduit and a cup portion shaped to form said sucking opening having a ring-shaped structure to define a receiving space therewith, wherein said scrubbing surface of said abrasion head is coaxially positioned within said receiving space.

10. A tissue removal pen, as recited in claim 9, wherein said vacuuming source comprises a vacuum pump device and an extension tube connected said vacuum pump device to a discharging end of said collecting conduit in such a manner that said vacuum pump device is arranged to provide said reduced pressure through said sucking opening of said collecting head for collecting said cells from said treating skin surface.

11. A tissue removal pen, as recited in claim 10, further comprising a motor assembly comprising a motor securely supported in said pen body and electrically connected to a power source via a conductive wire and a motor shaft operatively extended from said motor to said abrasion head, so as to provide an abrasion movement of said scrubbing surface of said abrasion head.

12. A tissue removal pen, as recited in claim 11, wherein said extension tube is constructed by two tubular holders integrally extended side by side wherein said first tubular holder is integrally connected to said discharging end of said collecting conduit for communicating said vacuum pump device with said collecting head, and wherein said conductive wire is extended from said motor to said power source through said second tubular holder.

13. A tissue removal pen, as recited in claim 9, wherein said vacuuming source further comprises a control switch comprising a pusher arm transversely mounted on said pen body in a slidably movable manner for transversely biasing against said collecting conduit and a switch body extended from said pusher arm for driving said pusher to a position that when said pusher arm is moved toward said collecting conduit to bias against said collecting conduit, a pressure through said sucking opening is reduced, and when said pusher arm is moved away from said collecting conduit, said pressure through said sucking opening is increased.

14. A tissue removal pen, as recited in claim 3, wherein said vacuuming source comprises a vacuum pump device and an extension tube connected said vacuum pump device to a discharging end of said collecting conduit in such a manner that said vacuum pump device is arranged to provide said reduced pressure through said sucking opening of said collecting head for collecting said cells from said treating skin surface.

15. A tissue removal pen, as recited in claim 14, further comprising a motor assembly comprising a motor securely supported in said pen body and electrically connected to a power source via a conductive wire and a motor shaft operatively extended from said motor to said abrasion head, so as to provide an abrasion movement of said scrubbing surface of said abrasion head.

16. A tissue removal pen, as recited in claim 15, wherein said extension tube is constructed by two tubular holders integrally extended side by side wherein said first tubular holder is integrally connected to said discharging end of said collecting conduit for communicating said vacuum pump device with said collecting head, and wherein said conductive wire is extended from said motor to said power source through said second tubular holder.

17. A tissue removal pen, as recited in claim 3, wherein said vacuuming source further comprises a control switch comprising a pusher arm transversely mounted on said pen body in a slidably movable manner for transversely biasing against said collecting conduit and a switch body extended from said pusher arm for driving said pusher to a position that when said pusher arm is moved toward said collecting conduit to bias against said collecting conduit, a pressure through said sucking opening is reduced, and when said pusher arm is moved away from said collecting conduit, said pressure through said sucking opening is increased.

18. A tissue removal pen, as recited in claim 1, wherein said collecting head has an adapter portion detachably mounted to said intake end of said collecting conduit and a cup portion having a bell-shaped to form said sucking opening having an enlarged circular sucking area, wherein said scrubbing surface of said abrasion head is positioned adjacent to said sucking opening.

19. A tissue removal pen, as recited in claim 1, wherein said collecting head has an adapter portion detachably mounted to said intake end of said collecting conduit and a cup portion shaped to form said sucking opening having an U-shaped structure so as to define a receiving space, wherein said scrubbing surface of said abrasion head is positioned within receiving space.

20. A tissue removal pen, as recited in claim 1, wherein said collecting head has an adapter portion detachably mounted to said intake end of said collecting conduit and a cup portion shaped to form said sucking opening having a ring-shaped structure to define a receiving space therewith, wherein said scrubbing surface of said abrasion head is coaxially positioned within said receiving space.

* * * * *